(12) United States Patent
Bovolenta et al.

(10) Patent No.: US 9,133,481 B2
(45) Date of Patent: Sep. 15, 2015

(54) SEMI-STABLE PRODUCTION OF LENTIVIRAL VECTORS

(75) Inventors: Chiara Bovolenta, Milan (IT); Anna Stornaiuolo, Milan (IT); Paolo Rizzardi, Milan (IT); Fulvio Mavilio, Evry (FR)

(73) Assignee: MolMed S.p.A., Milan (IT)

( * ) Notice: Subject to any disclaimer, the term of this patent is extended or adjusted under 35 U.S.C. 154(b) by 241 days.

(21) Appl. No.: 13/819,989

(22) PCT Filed: Sep. 1, 2011

(86) PCT No.: PCT/EP2011/065089
§ 371 (c)(1),
(2), (4) Date: Feb. 28, 2013

(87) PCT Pub. No.: WO2012/028680
PCT Pub. Date: Mar. 8, 2012

(65) Prior Publication Data
US 2013/0164840 A1    Jun. 27, 2013

(30) Foreign Application Priority Data
Sep. 2, 2010   (EP) .................................... 10175088

(51) Int. Cl.
*C12N 15/63* (2006.01)
*C12N 15/86* (2006.01)
*C12N 15/867* (2006.01)

(52) U.S. Cl.
CPC ............. *C12N 15/86* (2013.01); *C12N 15/8673* (2013.01); *C12N 2710/14144* (2013.01); *C12N 2740/16052* (2013.01); *C12N 2750/14143* (2013.01); *C12N 2800/40* (2013.01); *C12N 2800/50* (2013.01)

(58) Field of Classification Search
None
See application file for complete search history.

(56) References Cited

FOREIGN PATENT DOCUMENTS

WO    WO 2012/028681 A1    3/2012

OTHER PUBLICATIONS

Ansorge, S., et al., "Recent progress in lentiviral vector mass production," *Biochemical Engineering Journal* 48:362-377, Elsevier B.V., Netherlands (2009).
Berns, K.I. and Linden, R.M. "The cryptic life style of adeno-associated virus," *BioEssays* 17(3): 237-245, ICSU Press, United States (1975).
Berns, K.I., et al., "Study of the Fine Structure of Adeno-Associated Virus DNA with Bacterial Restriction Endonucleases," *Journal of Virology* 16(13):712-719, American Society for Microbiology, United States (1975).
Bestor, T.H., "Gene silencing as a threat to the success of gene therapy," *The Journal of Clinical Investigation* 105(4):409-411, American Society for Clinical Investigation, United States (2000).
Broussau, S., et al., "Inducible Packaging Cells for Large-scale Production of Lentiviral Vectors in Serum-free Suspension Culture," *Molecular Therapy* 16(3):500-507, The American Society of Gene Therapy, United States (2008).
Carroll, R., et al., "A Human Immunodeficiency Virus Type 1 (HIV-1)-Based Retroviral Vector System Utilizing Stable HIV-1 Packaging Cell Lines," *Journal of Virology* 68(9):6047-6051, American Society for Microbiology, United States (1994).
Cheung, A.K.M., et al., "Integration of the Adeno-Associated Virus Genome into Cellular DNA in Latently Infected Human Detroit 6 Cells," *Journal of Virology* 33(2):739-748, American Society for Microbiology, United States (1980).
Cockrell, A.S., et al., "A *Trans*-Lentiviral Packaging Cell Line for High-Titer Conditional Self-Inactivating HIV-1 Vectors," *Molecular Therapy* 14(2):276-284, The American Society of Gene Therapy, United States (2006).
Corbeau, P., et al., "Efficient gene transfer by a human immunodeficiency virus type 1 (HIV-1)-derived vector utilizing a stable HIV packaging cell line," *Proc Natl Acad Sci USA* 93:14070-14075, National Academy of Sciences, United States (1996).
Di Nunzio, F., et al., "Transduction of Human Hematopoietic Stem Cells by Lentiviral Vectors Pseudotyped with the RD114-TR Chimeric Envelope Glycoprotein," *Human Gene Therapy* 18:811-820, Mary Ann Liebert, Inc., United States (2007).
Dull, T., et al., "A Third-Generation Lentivirus Vector with a Conditional Packaging System," *Journal of Virology* 72(11):8463-8471, American Society for Microbiology, United States (1998).
Follenzi, A., et al., "Gene transfer by lentiviral vectors is limited by nuclear translocation and rescued by HIV-1 *pol* sequences," *Nature Genetics* 25:217-222, Nature America Inc., United States (2000).
Ikeda, Y., et al., "Continuous high-titer HIV-1 vector production," *Nature Biotechnology* 21:569-572, Nature Publishing Group, England (2003).
Kaul, M., et al., "Regulated Lentiviral Packaging Cell Line Devoid of Most Viral *cis*-Acting Sequences," *Virology* 249:167-174, Academic Press, United States (1998).
Klages, N., et al., "A Stable System for the High-Titer Production of Multiply Attenuated Lentiviral Vectors," *Molecular Therapy* 2(2):170-176, Academic Press, United States (2000).
Ni, Y., et al., "Generation of a packaging cell line for prolonged large-scale production of high-titer HIV-$_1$-based lentiviral vector," *The Journal of Gene Medicine* 7:818-834, John Wiley & Sons, Ltd., England (2005).
Palombo, F., et al., "Site-Specific Integration in Mammalian Cells Mediated by a New Hybrid Baculovirus-Adeno-Associated Virus Vector," *Journal of Virology* 72(6):5025-5034, American Society for Microbiology, United States (1998).

(Continued)

*Primary Examiner* — Michele K Joike
(74) *Attorney, Agent, or Firm* — Sterne, Kessler, Goldstein & Fox PLLC (57) ABSTRACT

The present invention provides a new semi-stable packaging cell line and a method to produce lentiviral vectors (LV), using the semi-stable packaging cell line. New methods and packaging cell lines of the invention are generated using a baculo-AAV hybrid system for stable expression of structural and regulatory lentiviral proteins, such system comprising a baculoviral backbone containing an integration cassette flanked by AAV ITRs, in combination with a plasmid encoding rep protein. This system allows to obtain a stable integration of the structural and regulatory HIV-1 proteins gag/pol and rev. The system allows to obtain a cell line including the structural and regulatory HIV proteins gag/pol and rev, to be used for a semi-stable LV production.

19 Claims, 4 Drawing Sheets

(56) References Cited

OTHER PUBLICATIONS

Poeschla, E., et al., "Development of HIV vectors for anti-HIV gene therapy," *Proc Natl Acad Sci USA* 93:11395-11399, National Academy of Sciences, United States (1996).

Porcellini, S., et al., "Chim3 confers survival advantage to CD4+ T cells upon HIV-1 infection by preventing HIV-1 DNA integration and HIV-1-induced $G_2$ cell-cycle delay," *Blood* 115(20):4021-4029, The American Society of Hematology, United States (2010).

Porcellini, S., et al., "The F12-Vif derivative Chim3 inhibits HIV-1 replication in CD4+ T lymphocytes and CD34+-derived macrophages by blocking HIV-1 DNA integration," *Blood* 113(15):3443-3452, The American Society of Hematology, United States (2009).

Recchla, A., et al., "Site-Specific Integration of Functional Transgenes into the Human Genome by Adeno/AAV Hybrid Vectors," *Molecular Therapy* 10(4):660-670, The American Society of Gene Therapy, United States (2004).

Samulski, R.J., et al., "A Recombinant Plasmid from Which an Infectious Adeno-Associated Virus Genome Can Be Excised In Vitro and Its Use To Study Viral Replication," *Journal of Virology* 61(10):3096-3101, American Society for Microbiology, United States (1987).

Sandrin, V., et al., "Intracellular Trafficking of Gag and Env Proteins and Their Interactions Modulate Pseudotyping of Retroviruses," *Journal of Virology* 78(13):7153-7164, American Society for Microbiology, United States (2004).

Sandrin, V., et al., "Lentiviral vectors pseudotyped with a modified RD114 envelope glycoprotein show increased stability in sera and augmented transduction of primary lymphocytes and CD34+ cells derived from human and nonhuman primates," *Blood* 100(3):823-832, The American Society of Hematology, United States (2002).

Schambach, A. and Baum, C., "Clinical Application of Lentiviral Vectors—Concepts and Practice," *Current Gene Therapy* 8:474-482, Bentham Science Publishers Ltd., Netherlands (2008).

Sena-Esteves, M., et al., "Generation of stable retrovirus packaging cell lines after transduction with herpes simplex virus hybrid amplicon vectors," *The Journal of Gene Medicine* 4:229-239, John Wiley & Sons, Ltd., England (2002).

Smith, R.H., "Adeno-associated virus integration: virus versus vector," *Gene Therapy* 15:817-822, Nature Publishing Group, England (2008).

Srinivasakumar, N., et al., "The Effect of Viral Regulatory Protein Expression on Gene Delivery by Human Immunodeficiency Virus Type 1 Vectors Produced in Stable Packaging Cell Lines," *Journal of Virology* 71(8):5841-5848, American Society for Microbiology, United States (1997).

Throm, R.E., et al., "Efficient construction of producer cell lines for a SIN lentiviral vector for SCID-X1 gene therapy by concatemeric array transfection," *Blood* 113(21):5104-5110, The American Society of Hematology, United States (2009).

Yu, H., et al., "Inducible Human Immunodeficiency Virus Type 1 Packaging Cell Lines," *Journal of Virology* 70(7):4530-4537, American Society for Microbiology, United States (1996).

Zufferey, R., et al., "Multiply attenuated lentiviral vector achieves efficient gene delivery in vivo," *Nature Biotechnology* 15:871-875, Nature Publishing Group, England (1997).

International Search Report, mailed Dec. 22, 2011, for International Application No. PCT/EP2011/065089, filed Sep. 1, 2011.

International Search Report, mailed Dec. 22, 2011, for International Application No. PCT/EP2011/065090, filed Sep. 1, 2011.

Non-published co-pending U.S. Appl. No. 13/819,991, 371 (c) date Oct. 15, 2013.

SEMI-STABLE PRODUCTION OF LENTIVIRAL VECTORS

CROSS-REFERENCE TO RELATED APPLICATIONS

The present application is a U.S. National Phase of International Application No. PCT/EP2011/065089, filed Sep. 1, 2011, which claims the benefit of European Application No. 10175088.3, filed Sep. 2, 2010, each of which is incorporated herein by reference in its entirety.

REFERENCE TO SEQUENCE LISTING SUBMITTED ELECTRONICALLY

The content of the electronically submitted sequence listing (Name: 181WOPA_Seq_Lis.txt; Size: 4,045 bytes; and Date of Creation: Feb. 28, 2013) filed herewith is incorporated herein by reference in its entirety.

FIELD OF THE INVENTION

The present invention relates to the production of lentiviral vectors (LV) for gene therapy. More particularly, the invention relates to semi-stable lentiviral packaging cell lines and methods of manufacturing packaging cell lines using an hybrid baculo-Adeno associated virus (AAV) vector for stable integration of structural and regulatory lentiviral proteins.

BACKGROUND

Since the first-ever LV phase I clinical trial against AIDS in 2001, 38 phase I-II and two phase II-III trials exploiting HIV-based LV as gene delivery vehicles have undergone authorities' scrutiny; three of them are still under review. The largest number of trials comprises monogenic disorders, some of which with large incidence such as Cooley's anemia β-thalassemia major (4 trials). Cancer and infectious diseases, mostly HIV-1 infection, follow. Commonly, the number of patients enrolled in phase I/II trials is limited, but not that in phase III. Thus stable packaging cell lines for $2^{nd}$ (LTR-based) and $3^{rd}$ (SIN-based) LV generation are urgently needed to cope LV large scale production demand for phase III trials hopefully attainable in the future in a larger number. LV production grounded on transient protocols is indeed impractical for global application under a safety, cost and reproducibility standpoint.

An increasing body of evidence indicates that LV, the most recently developed viral integrating vectors for gene therapy, are broadly applicable to transduce either terminally differentiated or cycling cells, ideal to sustain long-term transgene expression and safer than what was initially feared. The experience accumulated on Moloney murine leukemia virus (Mo-MLV) gamma-retroviral vectors (γRV) over the last two decades guided the fast progress on LV delivery system, whose development originated by the necessity of overcoming the inability of retrovirus to transduce non diving cells. In particular, the generation of self-inactivating (SIN) transfer vectors makes the prospect of a large use of LV in human clinical trials more feasible[1] provided the expansion and optimization of an as much efficient manufacturing process. However, in contrast to γRV, which can be produced by several human and murine commercially available packaging cell lines, LV are currently produced not only for research-grade, but also for GMP-grade, almost exclusively by transient transfection. This technology is expensive, difficult to standardize and scale-up and requires numerous downstream validation tests. Furthermore, the risk of replication competent lentiviruses (RCL), possibly arising through recombination between viral sequences in the packaging and transfer vector constructs, is a rare, but more likely event during transient than stable production.

The development of a retroviral-equivalent stable packaging cell line for LV turned out to be slower and more difficult because, as opposite to gamma retrovirus, the expression of lentiviral proteins, such as the env, protease, and some accessory proteins is toxic for human cells. To overcome this problem the accessory genes, present in the very early versions of packaging cells, were later removed in the latest generations. First generation SIV- and HIV-based LV packaging cell lines were obtained from either monkey Vero, or human COS, HeLa and 293 adherent cells[2-5], engineered with lentivirus genomes carrying few crucial modifications such as the removal of the packaging signal. The gp120 env and most accessory genes were in fact maintained. The resulting LV titer was very low[2-5], and more importantly the possible application of these vectors was necessarily restricted to CD4+ T cells for anti-AIDS gene therapy approaches. Later, gp120 env was substituted with the glycoprotein derived from the vesicular stomatitis virus (VSV-G) and all accessory genes were removed because proven dispensable for an efficient LV production. To prevent the toxicity also described for VSV-G, its expression was conditionally induced by a variety of different systems, such as the Tet, ecdysone, Rev and the combination of Tet and cumate[6]. Similarly, to reduce the toxic effect of the viral protease during clone selection, the conditional expression of the gag-pol gene by the Tet and the combination of doxycycline and cumate drugs have been described[6]. In all these systems gag-pol, rev and env genes were integrated by transient transfection of plasmid DNA, followed by drug selection and cell cloning.

One of the crucial issue for the implementation of a truly stable packaging cell line is the choice of the best viral gene delivery vehicles. Most researchers integrated the gag-pol, rev and env genes by transient transfection of plasmid DNA, followed by drug selection and cell cloning[2-9]. This technology is known to suffer over time from gene silencing and gene loss[10], which can both jeopardize the long-term stability of the packaging clone.

Alternative gene delivery vehicles have been disclosed particularly in STAR[11] and in the more recently developed GPRG-TL-20[12] packaging cell lines where the gag, pol, and rev genes were integrated into HEK293T cells by MLV-shuttle vectors. Two copies of the recoded gag-pol gene were stably integrated in STAR, whereas no such information is available for GPRG-TL-20[12]. As opposite to STAR, where the env gene were transfected, in GPRG-TL-20 all the remaining viral genes were introduced by SIN-MLV.

Several systems exist that allow stable integration of foreign genome into host cells. Palombo et al., 1998[13] disclose an hybrid baculovirus-AAV vector for specific integration into host cells. Such vector appears to be very effective if it includes rep gene in the same hybrid baculovirus-AVV vector. There is no mention in this reference of the construct of the present invention let alone the suggestion of using this kind of system for LV production.

Over the last almost two decades, several attempts to generate stable LV packaging cell lines have been made. Despite the different technology disclosed, as of today none of these packaging cell lines is employed in clinical trials or corners the market yet. Therefore there is a need of new systems for large scale production of LV that are effective in terms of production capability and are safe, cost effective and reproducible.

SUMMARY OF THE INVENTION

The present invention is related to the field of production of LV. Several gene therapy clinical trials are ongoing employing LV as gene delivery vehicles. In all these trials LV production is still based on transient protocols.

The present invention provides a new strategy to generate an HIV-1-based packaging cell line. Such strategy is based on the use of a hybrid vector comprising baculoviral backbone containing an integration cassette flanked by AAV inverted terminal repeats (ITRs), the so-called baculo-AAV hybrid system, in combination with a plasmid encoding a rep protein. This system allows to obtain a stable integration of structural and regulatory HIV-1 proteins gag/pol and rev. The system of the present invention includes a) a hacuio-AAV hybrid vector characterized in that it contains two expression cassettes, one encoding lentiviral gag and pol genes and the other lentiviral rev and a selection marker, and b) a plasmid encoding a rep protein. The proposed system represents a new and advantageous way to deliver structural and regulatory HIV proteins in order to stably and effectively engineer host cells with structural lentiviral proteins. Using this system, it was obtained a first intermediate including only structural and regulatory HIV proteins gag/pol and rev, to be used for a semi-stable LV production, or as starting point to obtain $2^{nd}$ and $3^{rd}$ generation packaging cell lines including optionally the regulatory protein (Tat) and the envelope protein of interest, as well as producer cell lines including also the transfer vector.

The first intermediate carries two copies of the recombinant baculo-AAV packaging construct expressing the HIV-1 gag-pol and rev genes in a tri-cistronic configuration. Such intermediate has been called PK-7 and is referred to as PK-7 in the examples. Genome integration of baculo-AAV packaging vector was facilitated by the transient expression of the AAV Rep78 protein known to be necessary for an ITR-mediated AAV vector integration[14]. Such first intermediate showed to have a surprising genetic stability for 1 year of culture that has proven the continuous production of functional LV after transient transfection of the remaining genetic elements. In addition, no silencing phenomenon have been observed in such cells. Furthermore, by exactly mapping the integration site of the two tandernly integrated packaging AAV vectors in a non-coding intergenic transcriptionally active region, we have provided a safety argument against the possible activation of dangerous genes whose mRNA can be incorporated in the LV and, eventually, in the host target cells.

The developed packaging system based on the use of an hybrid baculo-AAV vector for stable expression of lentiviral gag-pol and rev has been called "MolPack". The expression system used in the present invention advantageously allows stable and safe introduction of structural (gag/pol) and regulatory (rev) HIV proteins, in only one transfection and cloning round. The production of LV currently employed in clinical trials is still based on transient transfection of all required proteins. On the contrary, the intermediate obtained with the expression system of the present invention is stable, does not show silencing phenomena, allows to develop a semi-stable production of LV with strong advantages from the economic point of view. In fact, the semi-stable production requires a reduced number of constructs to be transfected to obtain the final product. In addition, it has also remarkably found that, using the semi-stable production of the present invention, only one third of the DNA amount employed in the production with transient transfection is sufficient to obtain LV having a titer comparable to that of transiently produced LV. Moreover, the reduced number of constructs to be transfected reduces the possibility of recombination events with the formation of RCL, thus rendering lentiviral particle production safer. Therefore, the expression system, the semi-stable packaging cell line and the production method of the present invention are very advantageous in respect to tools and methods currently applied in clinical trials.

STATEMENTS OF THE INVENTION

According to a first aspect of the invention there is provided a system for stable expression of lentiviral structural and regulatory proteins consisting of:
  i. An hybrid vector comprising baculoviral backbone containing an integration cassette flanked by AAV ITRs including two expression cassettes, wherein the first expression cassette encodes lentiviral gag and pol genes and the second one lentiviral rev and a selection marker and
  ii. An expression plasmid containing the AAV rep Open Reading Frame (ORF) under control of a promoter.

Preferably the two expression cassettes of the hybrid vector are tail-to-tail oriented and each one is driven by a constitutive promoter and a poly A, preferably the promoter is selected from CMV, CMV IE, PGK, SV40, eF1α SFFV and RSV more preferably the promoter is a CMV IE promoter.

Preferably the selection marker is selected from hygromycin, kanamycin, neomycin, zeomycin resistance gene, more preferably the selection marker is hygromycin resistance gene.

More preferably the selection marker is cloned downstream an internal ribosome entry site (IRES). According to another aspect of the invention, there is provided a semi-stable lentiviral packaging cell line consisting of cells stably expressing lentiviral gag pol and rev characterized in that such cells contain stably integrated into its genome at least one copy of an integration cassette flanked by AAV ITRs including two expression cassettes, wherein the first expression cassette encodes lentiviral gag and pol genes and the second one lentiviral rev and a selection marker.

Preferably the cell is a human cell line preferably selected from HEK293, HEK293-T, HEK293-SF, TE671, HT1080 or HeLa, more preferably the cell line is HEK293-T.

Preferably the two expression cassettes are tail-to-tail oriented and each one is driven by a constitutive promoter and a poly A; preferably the promoter is selected from CMV, CMV IE, PGK, SV40, eF1α, SFFV and RSV, more preferably the constitutive promoter is a CMV IE promoter.

Preferably the selection marker is selected from hygromycin, kanamycin, neomycin, zeomycin resistance gene; more preferably the selection marker is hygromycin resistance gene. More preferably the selection marker is cloned downstream an IRES.

Preferably the AAV rep protein is selected from rep78 or rep68. More preferably rep protein is rep78. According to another aspect there is provided a method for producing lentiviral vectors comprising:
  i. Culturing a semi-stable lentiviral packaging cell line consisting of cells stably expressing lentiviral gag, pol and rev characterized in that such cells contains, stably integrated into its genome, at least one copy of an integration cassette flanked by AAV ITRs including two expression cassettes, wherein the first expression cassette encodes lentiviral gag and pol genes and the second one lentiviral rev and a selection marker ii. Inserting in the semi-stable packaging cell line an env gene iii. Inserting in the semi-stable packaging cell line a transfer vector Preferably the two expression cassettes are tail-to-tail oriented and each one is driven by a constitutive promoter and a poly A; preferably the promoter is selected from CMV, CMV IE, PGK, SV40, eF1α, SFFV and RSV, more preferably the constitutive promoter is a CMV IE promoter.

Preferably the selection marker is selected from hygromycin, kanamycin, neomycin, zeomycin resistance gene; more preferably the selection marker is hygromycin resistance gene. More preferably the selection marker is cloned downstream an IRES.

Envelope protein can be inserted in host cells using AAV vector, retroviral vector, stable plasmid integration or homologous recombination. Preferably the env gene is inserted by transient transfection using a plasmid.

Preferably the env gene is selected from VSV-G env, MLV 4070 env, RD114 env, chimeric envelope protein RD114-TR, chimeric envelope protein RD114pro, baculovirus GP64 env or GALV env or derivatives thereof, more preferably the env gene is the gene encoding the RD114-TR.

Preferably the transfer vector is inserted with a SIN lentiviral vector.

DETAILED DESCRIPTION OF THE INVENTION

A detailed description of preferred features and embodiments of the invention will be described by way of non-limiting example.

The invention can be put into practice by a person of ordinary skill in the art who will employ, unless otherwise indicated, conventional techniques of chemistry, molecular biology, microbiology, recombinant DNA and immunology. All such techniques are disclosed and explained in published literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); Current Protocols in Immunology, ch. 12, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. All these publications are incorporated by reference.

Baculo-AAV Hybrid System

The present invention provides a new strategy to generate an HIV-1-based packaging cell line. Optimization of production system for LV is one of the critical issues that needs to be solved for the development of gene therapy medicine based on LV technology. Despite the growing number of clinical trials employing this technology, LV are still produced, in such trials, using transient transfection protocols. In this way, production of LV is still very expensive and unsatisfactory for larger number of patients. For this reason, many efforts have been made to develop stable packaging cell lines for LV. One of the critical issues in the development of a stable lentiviral packaging cell line is choosing the right vehicle for engineering host cells. In many cases host cells have been engineered using plasmids, but, in such cases, genome instability and gene silencing phenomena have also been observed. Retroviral vectors have been used to stably integrate gag/pol and rev genes in two other cases. None of the stable packaging cell line developed so far has been employed in clinic.

The strategy of the present invention is based on the use of a system for stable expression of lentiviral structural and regulatory HIV proteins consisting of an hybrid vector comprising a baculoviral backbone containing an integration cassette flanked by AAV ITRs including two expression cassettes, wherein the first expression cassette encodes lentiviral gag and pol genes and the second one lentiviral rev and a selection marker; together with an expression plasmid containing the AAV rep ORF under control of a promoter. The presence of baculoviral backbone allows to host a big and complex integration cassette including two expression cassettes encoding several different proteins. The resulting baculo-AAV packaging vector allows to engineer host cells with viral proteins that are necessary to stably and effectively produce LV, through only one infection event.

Genome integration of baculo-AAV packaging vector was obtained by the transient expression of the AAV rep protein. This system allowed to obtain integration of AAV vectors in a non-coding intergenic transcriptionally active region, thus excluding activation of dangerous genes whose mRNA can be incorporated in the LV and eventually in the host target cells.

The proposed system represents a new and advantageous way to stably and effectively engineer host cell with structural and regulatory lentiviral proteins.

In a preferred embodiment, the two expression cassettes included in the baculo-AAV packaging construct are tail-to-tail oriented and each one is driven by a constitutive promoter and a poly A, preferably the promoter is selected from CMV, CMV IE, PGK, SV40, eF1α, SFFV, and RSV, more preferably the promoter is a CMV IE promoter. According to a preferred aspect of the invention, the selection marker included in the AAV packaging vector is selected from hygromycin, kanamycin, neomycin, zeomycin resistance gene; preferably the marker is hygromycin resistance gene; more preferably, the selection marker is cloned downstream an IRES.

Genome integration of baculo-AAV packaging vector was obtained by the transient expression of AAV Rep protein for an ITR-mediated AAV vector integration. In a preferred embodiment rep protein is selected from rep78 and rep68, more preferably the protein is rep78.

Using this system, it was possible to obtain cells engineered to stably express HIV-1 proteins gag/pol and rev, such cells are called semi-stable packaging cell line. Particulariy, the present invention discloses and claims such engineered cells and their use for a semi-stable LV production.

Semi-stable Packaging Cell Line

Semi-stable packaging cell line of the present invention consists of host cells carrying at least one copy of the recombinant baculo-AAV packaging construct expressing the HIV-1 gag-pol and rev genes. Genome integration of baculo-AAV packaging vector has been obtained by the transient expression of the AAV rep protein in order to obtain ITR-mediated AAV vector integration. Preferably the two expression cassettes are tail-to-tail oriented and each one is driven by a constitutive promoter and a poly A, preferably the promoter is selected from CMV, CMV IE, PGK, SV40, eF1α, SFFV and RSV. More preferably the constitutive promoter is a CMV IE promoter.

According to a preferred aspect of the invention the selection marker is selected from hygromycin, kanamycin, neomycin, zeomycin resistance gene; preferably the selection marker is hygromycin resistance gene, more preferably the selection marker is cloned downstream an IRES.

Preferably the AAV rep protein is selected from rep78 and rep68. More preferably rep protein is rep78. Host cell lines that can be engineered to obtain the semi-stable packaging cell line are human cell lines selected from HEK293, HEK293-T, HEK293-SF, TE671, HT1080 or HeLa, more preferably the cell line is HEK293-T.

Such semi-stable packaging cell line is suitable for the output of a potentially large variety of LV, with different env and different transfer vectors in a semi-stable production system. Therefore, it represents a great advantage for a more effective production of LV since it allows costs reduction, it does not require using the GMP-grade plasmid DNA encoding gag-pol and rev, and the risk of RCL formation secondary to recombination events between the plasmids during transient transfection is reduced. The semi-stable packaging cell line is a versatile tool, and is safer and economically more advantageous than other tools currently employed in clinical trials for the production of LV.

Semi-stable packaging cell line of the present invention showed to have a surprising genetic stability for 1 year of culture that has proven the continuous production of functional LV after transient transfection of the remaining genetic elements. In addition, no silencing phenomenon have been observed in fact, both titer and infectivity of LV obtained using this intermediate remained unaffected after 1 year. Such data were confirmed both in the presence or absence of selective pressure. Remarkably, no comparable data regarding the integration stability of an AAV-ITR mediated cassette are available in the literature. The only related information is that a human bone marrow derived, fibroblast-like cell line (Ruddle's Detroit 6 cells) infected with wild type AAV serotype 2 (AVV-2) maintained viral sequences in a latent state for at least 47 and 118 passages. As shown in the examples the semi-stable packaging cell line of the present invention survived for at least 102 passages.

Therefore, the present invention provides a method for producing LV comprising:
i. Culturing a semi-stable packaging cell line as described above
ii. Inserting in the semi-stable packaging cell line an env gene
iii. Inserting in the semi-stable packaging cell line a transfer vector Envelope protein can be inserted in host cells using AAV vector, retroviral vector, stable plasmid integration or homologous recombination. Preferably the env gene is inserted by transient transfection using a plasmid.

Preferably the env gene is selected from VSV-G env, MLV 4070 env, RD114 env, chimeric envelope protein RD114-TR, chimeric envelope protein RD114pro, baculovirus GP64 env or GALV env or derivatives thereof. More preferably the present invention makes use the chimeric envelope protein RD114-TR env in which the cytoplasmic tail of RD114 has been replaced by that of MLV envelope. Preferably the transfer vector is inserted with a SIN-LV.

Semi-stable packaging cell line of the present invention are able to produce LV that in terms of infectivity are "qualitatively" equal to those produced by transient transfection. A very important issue to be considered for the application of the semi-stable production of LV is that semi-stable packaging cell line did not lose the ability to be easily transfectable. In fact, PK-7 cells are transfected at the same level of the parental cell line HEK293T. This feature is quite commonly lost after genetic modification and cloning of HEK293 cells with packaging construct. On the contrary, the expression system employed in the present invention for stable integration of gag/pol and rev does not cause any problem to the transfectability of semi-stable packaging cell line.

Moreover, the semi-stable packaging cell line and its use in the production method for LV have important advantages for the production costs. Particularly, only three additional constructs, for example plasmids, (each encoding tat, env and transfer vector) are necessary for production of $2^{nd}$ generation LV, or two constructs (each encoding env and transfer vector) for production of $3^{rd}$ generation LV. On the contrary, GMP methods currently employed in clinical trials require the use of two additional constructs, encoding gag/pol and rev respectively, in addition to those used with the semi-stable packaging cell line of the present invention.

Further, the reduced number of constructs to be transfected with the methods and tools of the present inventions, also represents an additional advantage for the safety of the LV as described above.

Moreover, it was also notably found that, using the semi-stable production of the present invention, only one third of the total amount of DNA employed in the production by transient transfection is sufficient to obtain lentiviruses having a titer comparable to that of transiently produced lentiviruses. Therefore, the expression system, the semi-stable packaging cell line and the production method of the present invention are very advantageous in respect to tools and methods currently applied in the clinic.

DESCRIPTION OF THE FIGURES

FIG. 1 Schemes of RD-MolPack development. (a) Schematic representation of the DNA plasmids used in the study. pPolh, polyhedrin promoter; attB1, attachement B1; ITR, inverted terminal repeat; CMV, cytomegalovirus promoter; In, intron; RRE, rev responsive element; A, polyA sequence; IRES, internal ribosome entry site; SD, splice donor; SA, splice acceptor; Ψ, packaging signal; WPRE, woodchuck hepatitis post-transcriptional regulatory element; cPPT, central polypurine tract; hPGK, human posphoglycerate kinase promoter. (b) Cartoon of the Rep78-mediated genomic integration of the AAV-GPR vector. MV Rep78 promotes the excision of the ITR-flanked AAV-GPR cassette and facilitates its integration into human chromosomes. (c) Flow chart of the production by semi-stable packaging cell line. GOI, gene of interest.

FIG. 2 Characterization of the PK clones. (a) Southern blot analysis of the AAV-GPR vector integration. To establish the number of copies and the integrity of the cassette, genomic DNA (10 µg) derived from PK clones was digested with two different restriction enzymes, BamHI and SnaBI, respectively. (b) Western blot analysis of the viral proteins produced from the GPR cassette. Left panel, cell extracts (50 µg/lane) obtained from the PK clones were hybridized to an anti-HIV human serum recognizing HIV-1 proteins. The membrane was sequentially hybridized with an anti-rev specific Ab. Right panel, 30 ng p24gag-equivalent of viral like particles (VLP) produced from PK clones were processed identically to the cellular extracts. (c) Schematic mapping of the GPR-cassette integration by LM-PCR technique which identified the DNA break-point in the long arm of chromosome 2 at the 2q32.1 location. (d) Co-localization of the AAV-GPR cassette and the human Hox4 gene into chromosome 2. In situ hybridization of PK-7 metaphase chromosomes was carried out using a gag-specific (red) and a Hox4-specific (green) probe, respectively. (e) Schematic representation of the rearrangement of the two GPR integrated cassettes in the PK-7 clone and their tail-to-head orientation.

FIG. 3 Control experiments relative to the Baculo-AAV-GPR and Rep78 possible integration. (a) Southern blot analysis of the recombinant baculovirus-AAV DNA. DNA was extracted from baculovirus particles, digested overnight with MluI restriction enzyme and, after blotting, probed with the 11-kb GPR cassette specific probe. Entry-GPR plasmid (1 pg) and baculovirus empty DNA (100 ng) were loaded as positive and negative control, respectively. (b) Detection of putative residual rep78 plasmid DNA integration into PK-7 cells. Rep78 specific PCR was carried out using the PK-7 genomic DNA as sample template and the CMV-rep78 (1 pg) plasmid as positive control.

EXAMPLES

Example I

General Methods

Plasmids

Figure 1:
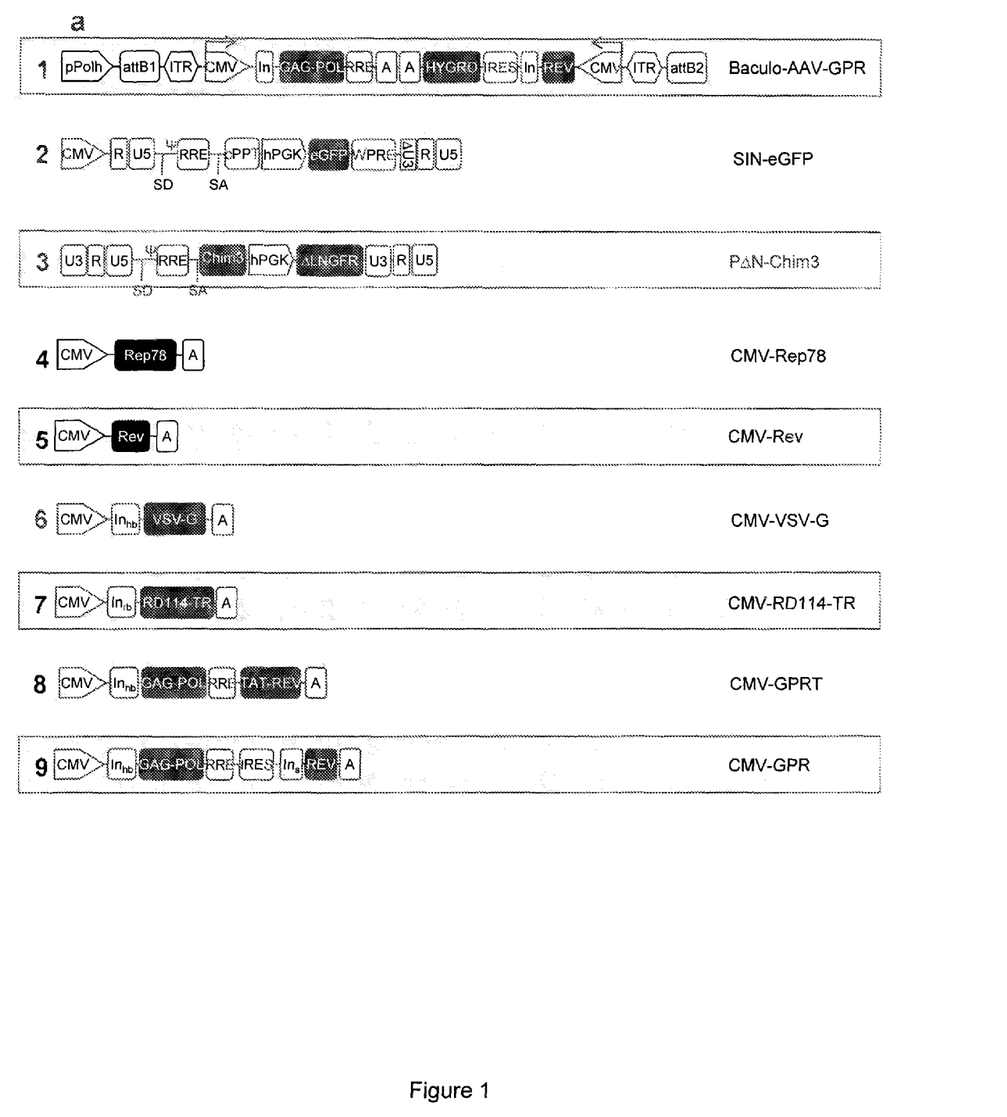

Wild-type HIV-1 gag, pol and rev genes were excised by MluI/NarI and MluI/NotI digestions from the pCG719-pKL-gagpol (hereafter named CMV-GPR for simplicity) (FIG. 1a, scheme 9) and pCG720-pKrev (CMV-Rev) (FIG. 1a, scheme 5) plasmids, respectively[25]. The viral genes were inserted into the Gateway® pENTR™4 shuttle vector (Invitrogen, Co., Carlsbad, Calif.) in two distinct expression cassettes tail-to-tail oriented, each cassette driven by a CMV IE promoter and carrying a polyA sequence. The first cassette expresses the gag and pol genes whereas the second one the rev gene and the selection marker hygromycin resistance (hygro) gene; hygro was cloned downstream an IRES to allow bi-cistronic translation. The two expression units were introduced into the XbaI site of the recombinant pSUB201 plasmid carrying an infectious AAV genome[17]. The resulting 5'ITR-CMV-gag-pol-polyA-polyA-hygro-IRES-rev-CMV-ITR3' cassette was then excised and inserted into the Gateway®pENTR™4 shuttle vector (Invitrogen, Co., Carlsbad, Calif.). The recombinant hybrid baculo-AAV packaging vector (Baculo-AAV-GPR) (FIG. 1a, scheme 1) was obtained by means of the bacteriophage lambda site-specific recombination system between the pENTR™4 shuttle entry vector, containing the two cassettes, and the BaculoDirect Linear DNA (BaculoDirect™ Baculovirus Expression Systems, Invitrogen, Co.). During homologous recombination the polyhedrin gene of the baculo DNA was thereby replaced with the GPR double cassette. The pABCMV-rep78 expression plasmid (CMV-AAV-rep78) was obtained by cloning the AAV-rep78 ORF under the CMV IE promoter of the expression vector pABS.43 as described in Recchia et al., 2004[18] (FIG. 1a, scheme 4). The pMD.G plasmid (CMV-VSV-G)[19], encodes the vesicular stomatitis envelope glycoprotein (VSV-G) (FIG. 1a, scheme 6). The $3^{rd}$-generation transfer vector, pCCLsin.PPT.hPGK.eGFP.WPRE.Amp (SIN-eGFP)[20] expresses the eGFP gene under the constitutive promoter hPGK (FIG. 1a, scheme 2). The $2^{nd}$-generation PΔN-Chim3 transfer vector expressing the anti-HIV-1 Chim3 transgene was described in Porcellini et al., 2009 & 2010[21,22] (FIG. 1a, scheme 3). The pCMV-RD114-TR (CMV-RD114-TR) (FIG. 1a, scheme 7) plasmid encodes the chimeric RD114-TR envelope, made of the extracellular and trans-membrane domains of the feline endogenous retrovirus RD114 envelope and the cytoplasmic tail (TR) of the A-MLVenv 4070A[23]. The $2^{nd}$-generation packaging pCMV-ΔR8.74 (CMV-GPRT) construct (FIG. 1a, scheme 8) encoding the HIV-1 gag, pol, rev and tat genes[19].

Cells

Spodoptera frugiperda (Sf9) insect cells (Invitrogen, Co.) were grown in suspension in TC-100 medium (Invitrogen, Co.) supplemented with 10% FCS (EuroClone Ltd, UK) and a combination of penicillin-streptomycin and glutamine (PSG) at 27° C. in the absence of $CO_2$. Human embryo kidney 293T (HEK293T) cells and its derivative clone (PK-7) were propagated in Dulbecco's Modified Eagle Medium (DMEM) supplemented with 10% FCS and PSG. CEM A3.01 and SupT1 T lymphoblastoid cells were grown in RPMI 1640 supplemented with 10% FCS and PSG. $CD34^+$ haemopoietic stem cells (HSC) and neonatal leukocytes were purified from umbilical cord blood (UCB) centrifugation on a Ficoll-Hypaque gradient (Lymphoprep, Nycomed Pharma AS, Oslo, Norway). After gradient separation, $CD34^+$ HSC were isolated from the collected UCB mononucleated cell ring by positive selection using CD34 MicroBeads Kit and Mini-MACS Separator Columns (Miltenyi Biotec, Sunnyvale, Calif.). $CD34^+$ cells purity (>92%) was established by FACS analysis (FACSCalibur BD Bioscience, San Jose, Calif.) and the FlowJo software (Tree Star, Inc., Ashland, Oreg.), using the anti-CD34-PE Ab (BD Pharmingen™, San Diego, Calif.). $CD34^+$ cells were pre-stimulated for 24 hours in 20% serum Iscove's Modified Dulbecco's Medium (IMDM) containing human stem cell factor (h-SCF) 100 ng/ml (R&D Systems, Minneapolis, Minn.), h-Flt3L 100 ng/ml (Peprotech, Rocky Hill, N.J.), h-IL-6 20 ng/ml (R&D Systems) and human thrombopoietin (h-Tpo) 20 ng/ml (Peprotech) and maintained in the same medium during transduction. Neonatal leukocytes were stimulated for 48 hours with the soluble anti-human CD3 (30 ng/ml) (Orthoclone OKT3, Janssen-Cilag, UK) and recombinant human IL-2 (rhIL-2) 50 U/ml (Chiron, Emeryville, Calif.) in RPMI and then kept in RPMI supplemented with 10% FCS, PSG, and rhIL-2.

Baculovirus Production and Baculo-GPIR Infection of HEK293T Cells

Baculovirus, carrying the recombinant hybrid Baculo-AAV-GPR DNA genome, was produced following the BaculoDirect method using the Gateway® adapted Baculovirus DNA system (Invitrogen, Co.). Recombinant Baculovirus titer was evaluated by plaque assay and corresponded to $1 \times 10^{11}$ pfu/ml after three passages of viral amplification in Sf9 cells. PK-7 clone was obtained by transfecting $1.5 \times 10^6$ HEK293T cells with 4 μg of AAV-rep78 expression plasmid and 24 hours afterwards infected with the recombinant Baculo-AAV-GPR at an MOI of 1,000. Cells were maintained without hygromycin for 4 days and then $5 \times 10^5$ cells were seeded in 22 10-cm dishes in the presence of hygromycin (100 μg/ml) at serially diluted concentrations. The 22 dishes were screened for p24gag production by ELISA. Only one dish, in which cells were seeded at $3.7 \times 10^4$ cells/dish, released sufficient p24gag in the supernatant. The dish contained 40 colonies which were all picked-up and screened. Three of them, scoring positive for p24gag production, were further characterized.

Lentiviral Vector (LV) Production and Titration

Pseudo-typed LVs produced from HEK293T cells were obtained by transient co-transfection of the following plasmids: the packaging constructs CMV-GPR ($3^{rd}$-generation) [or CMV-GPRT ($2^{nd}$-generation)], the VSV-G or RD114-TR envelope constructs, and the $3^{rd}$-generation SIN-eGFP[24] or the $2^{nd}$-generation PAN-Chim3 transfer vector[21]. The ratio of packaging:envelope:transfer vector was 6.5:3.5:10 μg DNA unless otherwise indicated. LV from PK-7 clone were generated by co-transfecting the env-expressing plasmid and the transfer vector. Transient transfections were performed with either the standard $Ca^{++}$-phosphate method or the Fugene™6 system following the manufacturer's instruction (Roche Diagnostics Corporation, Indianapolis, Ind.) obtaining similar results. Supernatants were harvested 48 hours after transfection and filtered through a 0.45-μm filter. Titer was calculated on SupT1, CEM A3.01, primary activated peripheral blood mononucleated cells (PBMC) and umbilical cord blood derived $CD34^+$ HSC depending on the type of experiments. Briefly, SupT1 and activated primary mononucleated cells were transduced by two cycles of spinoculation (1,240×g for 1 hour) in the presence of polybrene (8 μg/ml) (Sigma-Aldrich, St Louis, Mo.) separated by an overnight resting phase; $CD34^+$ HSCs were transduced for 24 hours on retronectin-coated plates (Takara Bio, Otsu, Japan) without polybrene. Transduction efficiency was monitored by flow cytometry analysis (FACS Calibur BD Bioscience, San Jose, Calif.) of eGFP expression (SIN-eGFP). or ΔLNFGR expression (PΔN-Chim3), as described in Porcellini et al., 2009 & 2010[21,22], using the FlowJo software (Tree Star, Inc., Ashland, Oreg.) Only transduction values ranging from 5 to 20% positive cells were used to calculate the titer of each LV preparation according to the following formula: TU=[number of cells×(% GFP/100)]/vol sup (in ml).

Southern Blot Assay

Genomic DNA (gDNA) was isolated by the QIAamp Mini kit (QIAGEN GmbH, Germany) according to manufacturer's instructions. Baculovirus DNA was extracted from viral particles by the QIAamp DNA micro kit (QIAGEN). After overnight digestion with the indicated restriction enzymes 10 μg of gDNA was run on 0.8% agarose gel, blotted by Southern capillary transfer onto nylon membranes (Duralon, Stratagene, Tex., USA) and then hybridized to $1\times10^6$ dpm/ml of $^{32}$P-random primed labeled either 600-bp CMV or 11-kb GPR cassette.

Analytical PCR Analysis

PCR analysis for screening of residual integration of the AAV-Rep78 plasmid into PK-7 cells was performed on 300 ng of genomic gDNAs using the set of primers: AAV-Rep78 forward: 5'-CGG GCT GCT GGC CCA CCA GG-3' (SEQ ID NO:1); AAV-Rep78 reverse: 5'-ATG CCG GGG TTT TAC GAG ATT GTG-3' (SEQ ID NO:2) and the following PCR conditions: 98° C. for 7 minutes, 30 cycles of 94° C. for 30 seconds, 66° C. for 30 seconds, and 72° C. for 1.5 minutes.

To establish the orientation of the two GPR cassettes, PCR amplification was performed on 300 ng gDNAs using the set of primers: rev forward: 5'-CTT GAG GAG GTC TTC GTC GC-3' (SEQ ID NO:3); beta-globin reverse: 5'-CCC TGT TAC TTC TCC CCT TCC-3' (SEQ ID NO:4); rev forward nested: 5'-TGT CTC CGC TTC TTC CTG CC-3' (SEQ ID NO:5); beta-globin nested reverse: 5'-TTA ACC ATA GAA AAG AAG GGG-3' (SEQ ID NO:6)and the following conditions: 94° C. for 2 minutes, 35 cycles of 94° C. for 30 seconds, 52° C. for 30 seconds, and 72° C. for 1.5 minutes.

p24gag ELISA

Physical LV production was measured in culture supernatants by the Alliance HIV-1 p24 Antigen ELISA kit (Perkin Elmer Life and Analytical Sciences, Inc. Waltham, Mass.) following manufacturer's instructions, with the assumption that 1 pg p24gag corresponds to $1\times10^4$ physical particles.

Western Blot Analysis

Whole-cell and nuclear extracts derived from PK-7 cells and viral proteins derived from isolated cell-free VLP or LV were prepared as previously described[21,22]. Proteins were size-fractionated by SDS-PAGE, and electroblotted to Hybond ECL nitrocellulose membranes (GE Healthcare, Life Sciences, UK Ltd, UK). Membranes were blocked in 5% low-fat dry milk, and then incubated with the appropriate primary Ab. The anti-HIV serum, obtained from an AIDS patient, was used at 1:2,000 dilution; the HIV-1 rev MoAb (Rev-6, sc-69730 S. Cruz Biotechnology, Inc., S. Cruz, Calif.) at 1:200 dilution. Ab binding was visualized by the enhanced chemiluminescence system ECL (ECL, Amersham) following manufactures's instructions.

LV DNA Copy Number Quantification by Real-Time Taq-Man PCR

The copy number of the integrated GPR vector was established by quantitative Taq Man PCR using an ABI Prism 7,900 FAST instrument (Applied Biosystems, Foster City, Calif.) and analyzed by SDS 2.3 software (Applied Biosystems). Genomic DNA (gDNA) was amplified with the following primers and probe derived from the gag gene: forward: 5'-ACA TCA AGC AGC CAT GCA AAT-3' (SEQ ID NO:7); reverse: 5'-ATC TGG CCT GGT GCA ATA GG-3' (SEQ ID NO:8); probe: FAM 5'-CAT CAA TGA GGA AGC TGC AGA ATG GGA TAG A-3' (SEQ ID NO:9) TAMRA. PCR conditions were the following: 2 minutes at 50° C. and 5 minutes at 95° C., followed by 40 cycles of 15 seconds at 95° C. and 15 seconds at 60° C., with an increment of 0.1° C./cycle.

Ligation-mediated (LM)-PCR

Genomic DNA was extracted from PK-7 cells by QIAamp DNA Mini Kit (QIAGEN) according to the manufacturer's instructions and digested with BglII and BamHI at 37° C. overnight. Ligation of an adaptor 76-bp oligonucleotide linker compatible with the 5'-GATC-3' sticky ends was performed under standard conditions. LM-PCR was carried out using the following couple of nested primers: the ITR forward: 16 s: 5'-GTA GCA TGG CGG GTT AAT CA-3' (SEQ ID NO:10), and 17 s/long nested: 5'-TTA ACT ACA AGG AAC CCC TAG TGA TGG-3' (SEQ ID NO:11); the linker reverse primers: Linker-1: 5'-GTA ATA CGA CTC ACT ATA GGG C-3' (SEQ ID NO:12)and Linker-2 nested: 5'-AGG GCT CCG CTT AAG GGA C-3' (SEQ ID NO:13). The linker sequences corresponded to 5'-GAT CGT CCC TTA AGC GGA GCC CTA TAG TGA GTC GTA TTA CCA GGG AAT TCG CCT CGG GAT ATC ACT CAG CAT AAT G-3' (SEQ ID NO:14). Two rounds of LM-PCR were carried out using AmpliTaq Gold DNA Polymerase (Applied Biosystems), each comprising 30 cycles (95° C. for 30 seconds, 52° C. for 30 seconds, 72° C. for 2 minutes). PCR amplicons were cloned using the TOPO® cloning kit (Invitrogen, Co.) and plasmid colonies carrying inserts of approximately 100-200-bp were selected for sequencing. Sequence homologies were identified by BLAST search, NCBI.

Fluorescence in situ Hybridization (FISH)

Metaphase chromosomes were obtained by treating PK-7 cells with colchicine (10 μg/ml) (Sigma #C9754) for 2 hours at 37° C. After phosphate buffer saline (PBS) washing, cells were kept in hypotonic solution (75 mM KCl) for 6 minutes at room temperature (RT), fixed with 4 washes of methanol/acetic acid (3:1) and then spread on a clean glass slide. Cytogenetic samples were denatured in 70% formamide solution for 2 minutes at 72° C., dehydrated by cold 70%, 85%, and 95% ethanol consecutive washes and then air dried. The specific probes were prepared as follows: the 13-kb plasmid DNA containing the GFR cassette was labeled using the Random Primed DNA Labeling Kit (Roche Applied Science, Indianapolis, Ind.) with SpectrurnOrange™-dUTP (Vysis, Inc., Downers Grove, Ill.), whereas the control 30-kb cosmid DNA containing the human hax4 gene was labeled using the FISHBright™ Nucleic Acid Labeling kit (Kreatech Biotechnology, Amsterdam, The Netherlands). Hybridization was performed by incubating 5 ng/µl of each probe in 250 µl of 50% formamide, 2×SSC, and 10% dextran sulfate and 50 ng/µl of human $C_0T$-1 DNA hybridization buffer (Invitrogen). Samples were coated with denatured probes for 10 minutes at 75° C., covered with Parafilm®M, and incubated overnight at 37° C. in a moist chamber. Samples were washed once in 0.4×SSC, pH=7 at 72° C. for 2 minutes, once in 4×SSC, pH=7 containing 0.0025% Tween-20 for 30 seconds at RT and twice in PBS 1× for 1 minute at RT. Slides were counterstained with 0.02 µg/µl of 49,6-diamidino-2-phenylindole (DAPI) (Sigma). Visualization and photographic images were taken with a Nikon 80i upright microscope (Nikon Instruments S.p.A., Italy) using the green (FITC) and spectrum orange (spectrum orange) filter illumination. Images were processed with Genikon software (Nikon).

Example II

Generation of the First Intermediate PK-7 Clone

Figure 3:
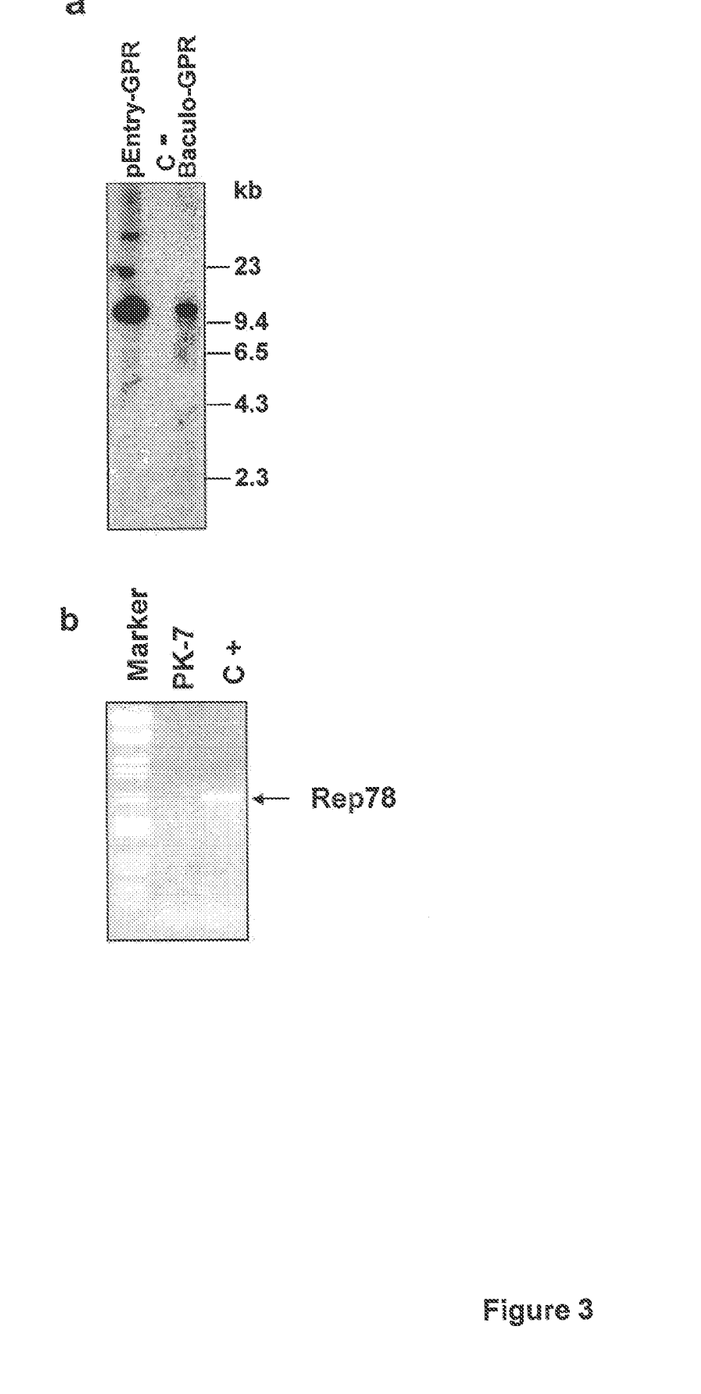

To obtain the RD-Mol Pack packaging cell line for the continuous production of either $2^{nd}$- or $3^{rd}$-generation LV, several HEK293T-derived intermediate clones were obtained. The first one was named PK-7 and was obtained by stable integration of HIV-1 gag, pol, and rev genes by means of the recombinant hybrid baculo-AAV vector (rhBaculo-AAV-GPR) (FIG. 1a, scheme 1). This delivery system exploits the integrase activity of AAV-rep78 protein, provided transiently, to excise and integrate the AAV ITR-flanked integration cassettes into human chromosomes (FIG. 1b). The rh-baculo-AAV vector was generated by homologous recombination between the BaculoDirect Linear DNA and the Gateway® pENTR™4 entry plasmid containing the ITR-flanked GPR cassettes (FIG. 1a, scheme 1). After 3 cycles (p3) of recombinant baculovirus amplification in Sf9 insect cells, the titer and the potential recombination events of the hybrid baculo-AAV DNA were checked by plaque assay and viral genomic DNA Southern blot, respectively. The titer at p3 corresponded to $6\times10^{10}$ pfu/ml, and Southern blot analysis revealed a single sharp band, demonstrating no recombination events during the virus amplification process (FIG. 3).

Figure 2:
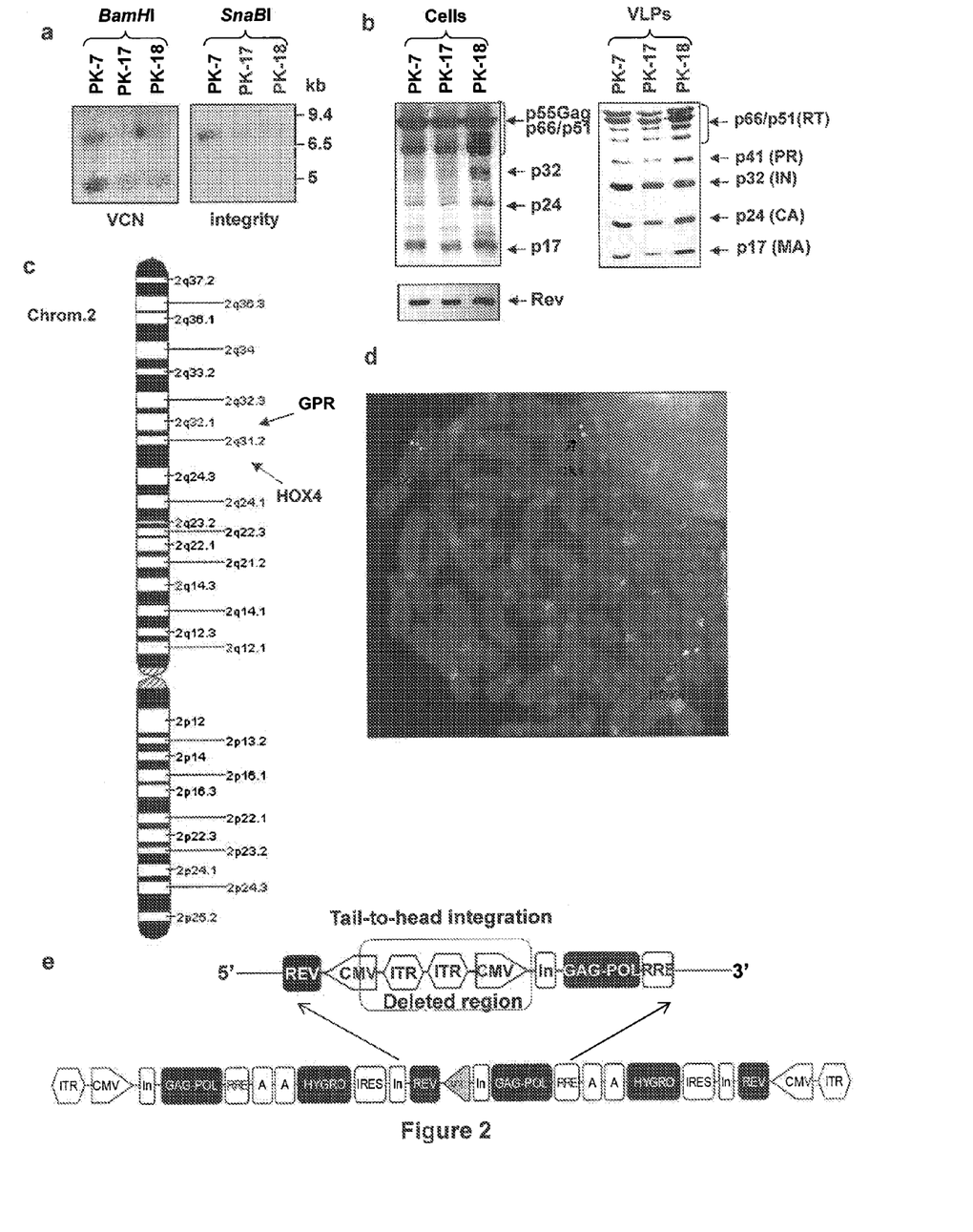

Next, the dose and time of AAV-Rep78 plasmid transfection and of rh-baculo-AAV infection and the cloning conditions of infected HEK293T cells were carefully defined (FIG. 1c). In fact, the choice of these experimental settings turned out to be critical. Thus after testing a wide-range of conditions, it was eventually established that a single dose of AAV-rep78 plasmid DNA transfected 24 hours before rh-baculo-AAV infection at the MOI of 1,000 corresponded to the best experimental design. Moreover, it was observed that seeding a total of $5\times10^5$ cells distributed in 22 90-mm-Petri dishes, each dish seeded at different concentration and adding hygromycin 100 µg/ml after 4 days from seeding was the best condition to collect the largest number of cell clones. Only three of the 360 counted clones, PK-7, PK-17 and PK-18, expressed p24gag above the 100 pg/ml settled threshold. Southern blot analysis of the clones revealed that each clone contains two copies of the correct-in-size vector (FIG. 2a). To exclude possible integration of residual AAV-rep78 plasmid DNA, rep78 specific PCR on PK-7 gDNA were carried out detecting no positive signal (FIG. 3b). The HIV-1 protein expression pattern derived from the GPR cassette was monitored by Western blot of the three PK clones and their matching viral like particles (VLP) released in the medium. All viral proteins were properly processed, correct-in-size and in the right, relative proportion (FIG. 2b). The future working PK clone was selected by calculating on SupT1 cells the potency of the LV produced from the three clones after being co-transfected with the VSV-G plasmid and the $3^{rd}$-generation transfer vector SIN-eGFP (Table 1). Of note, although the titer of control HEK293T LV produced by transient transfection was 5-fold higher than that of PK-7 and PK-18 LV, its infectivity was almost identical to that of the PK LV, suggesting that the PK clones generate LV that under a "quality" standpoint are comparable to those produced by conventional methods (Table 1). Although the potency of PK-7 and PK-18 LV was similar, PK-7 clone was selected for further genetic manipulation because its morphology, growth, viability and p24gag production values scored better than those of PK-18 clone (Table 1).

TABLE 1

Potency of VSV-G pseudotyped LV produced from PK clones

| Clones | Titer (TU/ml)[a] |
|---|---|
| PK-7[b] | 1.1 × 10⁷ |
| PK-17 | 5.4 × 10⁶ |
| PK-18 | 1.0 × 10⁷ |
| HEK-293T | 5.8 × 10⁷ |
| | p24Gag (ng/ml) |
| PK-7 | 406 |
| PK-17 | 636 |
| PK-18 | 326 |
| HEK-293T | 1694 |
| | Infectivity (TU/ng p24Gag) |
| PK-7 | 2.7 × 10⁴ |
| PK-17 | 8.4 × 10³ |
| PK-18 | 3.0 × 10⁴ |
| HEK-293T | 3.4 × 10⁴ |

[a]Titer was calculated on SupT1 cells 3 days after transduction. Cells were transfected with the VSV-G and SIN-eGFP plasmids.
[b]Bold indicates the selected clone.

Next, the integration of the ITR-flanked GPR cassette was characterized in depth in PK-7 clone by quantitative LM-PCR, TaqMan PCR (FIG. 2c) and FISH techniques (FIG. 2d). To exactly map the integration site, LM-PCR studies were carried out, which spotlighted the breakpoint at the chromosome 2, 2q32.1 (FIG. 2c). This result was confirmed by in situ hybridization with the specific GPR probe which revealed a single spot into chromosome 2 based on the arm length and centromere position (FIG. 2d). To confirm this location assignment, the HOX4 probe was used, which is known to map into chromosome 2q31.2. As HEK293T cells are triploid, HOX4 was rightly detected in all three chromosomes 2 (FIG. 2d). Lastly, it was confirmed by quantitative TaqMan PCR that two copies were integrated and by nested PCR with an appropriate design of the primers (FIG. 2e) that the two copies were in tandem orientation, tail-to-head. Tail-to-head orientation is the natural configuration observed also for the integration of wild type AAV and most rAAV vector concatamers into the host cell genome[16]. Sequence analysis of the amplicon encompassing the tail-to-head junction revealed that a 910-bp fragment comprising 303-bp of the 3' CMV promoter of the first cassette together with both ITRs of the first and second cassette and the entire 5' CMV promoter of the second cassette were lost (FIG. 2e, red box). The majority of the vector-cellular recombination events occurs in fact within the ITR sequences of the vector. This rearrangement has caused in the PK-7 cells the lack of transcription of the gag-pol gene of the second cassette and likely the lack of transcription of the rev and hygro genes of the first cassette.

However, it is worth mentioning that the 285-bp region left of the deleted CMV promoter (FIG. 2e, gray triangle in the center of the scheme) still contains the TATA box that might be sufficient to drive transcription of the rev and hygro genes. In conclusion, PK-7 contains two integrated cassettes, which collectively transcribe one gag-pol gene and one or two rev and hygro genes.

To demonstrate the stability of PK-7 clone over time, the cells were cultivated in the presence or absence of hygromycin for 350 days, corresponding to ca 420 cell doublings, and measured p24gag production on a per cell basis (Table 2). The average production in the presence of hygromycin corresponds to 15.34±8.47SD ng p24gag/1×10$^6$ cells, whereas in the absence of antibiotic is 6.70±3.51SD ng p24gag/1×10$^6$ cells (Table 2).

This difference likely derives from the fact that hygromycin drug pressure keeps on an "on" state the transcription of the hygro resistance gene and thereby the chromatin as well. This might favour the higher transcription of the gag-pol genes. To evaluate whether the VLP generated from PK-7 clone were functional even after hundreds of doublings, PK-7 cells were co-transfected at p60 and p102 with VSV-G envelope and SIN-eGFP transfer vector and calculated the LV potency on SupT1 cells. Remarkably, the titer and infectivity of LV produced both in the presence and absence of the selection drug persisted to normal level still after such prolonged time (Table 2). These data demonstrate no genetic instability of the GPR cassette regardless the presence or absence of drug pressure and allowed us to avoid the use of hygromycin in future characterization. No comparable data regarding the integration stability of an AAV-ITR mediated cassette are available in the literature. The only related information is that a human bone marrow derived, fibroblast-like cell line (Ruddle's Detroit 6 cells) infected with wild type AAV serotype 2 (AVV-2) maintained viral sequences in a latent state for at least 47 passages and 118 passages[22,23]. Notably, PK-7 cells survived for at least 102 passages.

TABLE 2

Stability of PK-7 clone over time

| Passage | Hygromycin p24Gag ng/10$^{6a}$ | No Hygromycin p24Gag ng/10$^{6a}$ |
|---|---|---|
| P2 | 10.00 | 8.10 |
| P6 | 7.00 | 4.80 |
| P10 | 11.40 | 4.00 |
| P16 | 5.00 | 4.80 |
| P20 | 9.30 | 5.20 |
| P24 | 7.20 | 6.50 |
| P28 | 9.20 | 4.40 |
| P32 | 6.20 | 8.80 |
| P36 | 11.00 | 9.60 |
| P40 | 18.00 | 10.00 |
| P44 | 4.30 | 8.40 |
| P48 | 37.50 | 3.80 |
| P52 | 7.00 | 3.20 |
| P56 | 11.00 | 6.70 |
| P60 | 19.00 | 4.40 |
| P64 | 22.00 | 18.70 |
| P68 | 15.20 | 8.00 |
| P72 | 16.50 | 4.90 |
| P76 | 17.80 | 7.60 |
| P80 | 30.00 | 11.00 |
| P84 | 27.00 | 8.40 |
| P88 | 23.20 | 3.50 |
| P92 | 23.00 | 7.50 |
| P98 | 16.70 | 1.36 |
| P102 | 19.00 | 3.85 |
| Mean ± SD | 15.34 ± 8.47 | 6.70 ± 3.51 |
| | Titer (TU/ml)$^b$ | |
| P60 | 3.2 × 10$^6$ | 2.0 × 10$^6$ |
| P102 | 2.7 × 10$^6$ | 1.3 × 10$^6$ |
| | p24Gag (ng/ml)$^b$ | |
| P60 | 86 | 38 |
| P102 | 80 | 13 |
| | Infectivity (TU/ng p24Gag)$^b$ | |
| P60 | 4.2 × 10$^4$ | 5.2 × 10$^4$ |
| P102 | 3.3 × 10$^4$ | 1.0 × 10$^5$ |

$^a$p24Gag level expressed as ng/1 × 10$^6$cells
$^b$Potency values of VSV-G pseudotyped LV produced after transfection of PK-7 cells with SIN-eGFP and VSV-G plasmids and tested on SupT1 cells 3 days after transduction Example III Use of PK-7 Clone for Semi-stable LV Production To better establish whether the semi-stable LV production from PK-7 clone was overall comparable to that of transient LV production from HEK293T cells, both cell types were transfected with the same amount of the necessary plasmids and measured the percentage of transfection and the potency of their respective LVs on different target cells (Table 3). In this condition, the mean of the percentage of transfection of 11 experiments with HEK293T cells was 90.54±3.6 SEM and that of 12 experiments with PK-7 cells was 91±5.3SEM, indicating that PK-7 cells maintain their high-level transfection capability. Then, the LV titer was calculated in SupT1 cells, as our standard reference cell type, cord blood derived CD34$^+$ HSC, and anti-CD3/IL-2 activated cord blood mononucleated cells (indicated as T lymph. in Table 3) (Table 3).

TABLE 3

Potency of VSV-G pseudotyped 3$^{rd}$ and 2$^{nd}$ generation LV produced from PK-7 clone calculated on different target cell types

| Vector | Producer | SupT1 | CD34$^+$ | T Lymph. |
|---|---|---|---|---|
| | | Titer (TU/ml) | | |
| SIN-eGFP | PK-7$^a$ | 5.7 × 10$^6$ | 2.4 × 10$^4$ | 2.3 × 10$^5$ |
| | HEK-293T$^b$ | 5.6 × 10$^7$ | 3.0 × 10$^5$ | 1.3 × 10$^6$ |
| | | p24Gag (ng/ml) | | |
| | PK-7 | 45 | 45 | 23 |
| | HEK-293T | 350 | 350 | 279 |
| | | Infectivity (TU/ng p24Gag) | | |
| | PK-7 | 1.2 × 10$^5$ | 5.3 × 10$^2$ | 1.0 × 10$^4$ |
| | HEK-293T | 1.6 × 10$^4$ | 8.6 × 10$^2$ | 4.6 × 10$^3$ |
| | | SupT1 | CD34$^+$ | CEM A3.01 |
| | | Titer (TU/ml) | | |
| PΔN-Chim3 | PK-7$^a$ | 2.2 × 10$^6$ | 1.4 × 10$^4$ | 3.7 × 10$^6$ |
| | HEK-293T$^b$ | 5.8 × 10$^6$ | 1.6 × 10$^4$ | 8.8 × 10$^6$ |

TABLE 3-continued

Potency of VSV-G pseudotyped 3$^{rd}$ and 2$^{nd}$ generation LV produced from PK-7 clone calculated on different target cell types

| | p24Gag (ng/ml) | | |
|---|---|---|---|
| PK-7 | 27 | 27 | 27 |
| HEK-293T | 114 | 114 | 114 |
| | Infectivity (TU/ng p24Gag) | | |
| PK-7 | $8.1 \times 10^4$ | $5.1 \times 10^2$ | $1.3 \times 10^5$ |
| HEK-293T | $5.0 \times 10^4$ | $1.4 \times 10^2$ | $7.7 \times 10^4$ |

$^a$VSV-G pseudotyped LV were produced after transfection of PK-7 cells with either the SIN-eGFP or the PΔN-Chim3 and VSV-G envelope plasmids.
$^b$VSV-G pseudotyped LV were produced after transfection of HEK-293T cells with CMV-GPR, SIN-eGFP (or PΔN-Chim3) and VSV-G envelope plasmids. LV were tested on target cells after 3-5 days of transduction.

Notably, the infectivity of 3$^{rd}$ generation LV, SIN-eGFP, generated from PK-7 cells was ca 1-log lower than and almost equal to that of control LV when the titer was calculated on SupT1 and CD34$^+$ cells, respectively, whereas half-log higher on activated T lymphocytes. The infectivity of the 2$^{nd}$ generation LV, PΔN-Chim3, generated from PK-7 cells was almost equal to that of control LV when the titer was calculated on either SupT1 cells or CD34$^+$ or CEM A3.01 cells. Collectively, these findings indicate that PK-7 clone produces LV "qualitatively" equal to those produced by transiently co-transfected HEK293T cells. A very important issue to be considered for the application of PK-7 in semi-stable production of LV is that PK-7 clone did not lose the ability to be easily transfectable. This feature is quite commonly lost after genetic modification and cloning of 293 cells with packaging construct.

Titration experiments were carried out to establish the dose of total DNA of the envelope plasmid and transfer vector to be used for optimal LV production from PK-7 cells. Notably, it was established that even less than one third of total amount of DNA (0.3 mg) was sufficient to generate LV with a titer comparable to that of LV produced with the standard amount of DNA (1 mg) on both SupT1 and CEM A3.01 cell lines. Therefore using PK-7 for semi-stable production of LV instead of HEK293T cells will dramatically cut the high cost of the GMP-grade plasmid DNA.

TABLE 4

Reduction of total amount of plasmid DNA (small-scale)

| | 0.3 mg | | 0.6 mg | | 1 mg | |
|---|---|---|---|---|---|---|
| Plasmid DNA | SupT1 | CEM A3.01 | SupT1 | CEM A3.01 | SupT1 | CEM A3.01 |
| Titer (TU/ml)$^a$ | $1.2 \times 10^7$ | $4.9 \times 10^6$ | $1.1 \times 10^7$ | $3.5 \times 10^8$ | $1.0 \times 10^7$ | $4.1 \times 10^8$ |
| p24Gag (ng/ml) | 111 | 111 | 105 | 105 | 85 | 85 |
| Infectivity (TU/p24Gag) | $1.0 \times 10^5$ | $4.4 \times 10^4$ | $1.0 \times 10^5$ | $3.3 \times 10^4$ | $1.1 \times 10^5$ | $4.8 \times 10^4$ |

$^a$Titer of LVs produced after transfection of PK-7 cells with PΔN-eGFP vector and VSV-G envelope.

References

1. Schambach A, Baum C. Clinical application of lentiviral vectors—concepts and practice. Curr Gene Ther. 2008; 8:474-482.
2. Carroll R, Lin J T, Dacquel E J, Mosca J D, Burke D S, St Louis D C. A human immunodeficiency virus type 1 (HIV-1)-based retroviral vector system utilizing stable HIV-1 packaging cell lines. J Virol, 1994; 68:6047-6051.
3. Vu H, Rabson A B, Kaul M, Ron V, Dougherty J P. Inducible human immunodeficiency virus type 1 packaging cell lines. J Virol. 1996; 70:4530-4537.
4. Poeschla E, Corbeau P, Wong-Staal F. Development of HIV vectors for anti-HIV gene therapy. Proc Natl Acad Sci USA. 1996; 93:11395-11399.
5. Corbeau P, Kraus G, Wong-Staal F. Efficient gene transfer by a human immunodeficiency virus type 1 (HIV-1)derived vector utilizing a stable HIV packaging cell line. Proc Natl Acad Sci USA. 1996; 93:14070-14075.
6. Broussau S, Jabbour N, Lachapelle G, et al. inducible packaging cells for large-scale production of lentiviral vectors in serum-free suspension culture. Mol Ther. 2008; 16:500-507.
7. Srinivasakumar N, Chazal N, Helga-Maria C, Prasad S, Hammarskjold M L, Rekosh D. The effect of viral regulatory protein expression on gene delivery by human immunodeficiency virus type 1 vectors produced in stable packaging cell lines. J Virol. 1997; 71:5841-5848.
8. Kaul M, Yu H, Ron Y, Dougherty J P. Regulated lentiviral packaging cell line devoid of most viral cis-acting sequences. Virology. 1998; 249:167-174.
9. Cockrell A S, Ma H, Fu K, McCown T J, Kafri T. A trans-lentiviral packaging cell line for high-titer conditional self-inactivating HIV-1 vectors. Mol Ther. 2006; 14:276-284.
10. Bestor T H. Gene silencing as a threat to the success of gene therapy. Clin Invest. 2000; 105:409-411.
11. Ikeda Y, Takeuchi Y, Martin F, Cosset F L, Mitrophanous K, Collins M. Continuous high-titer HIV-1 vector production. Nat Biotechnol. 2003; 21:569-572.
12. Throm R E, Ourna A A, Zhou S, et al. Efficient construction of producer cell lines for a SIN lentiviral vector for SCID-X1 gene therapy by concatemeric array transfection. Blood. 2009; 113:5104-5110.
13. Palombo F, Monciotti A, Recchia A, Cortese R, Ciliberto G, La Monica N. Site-specific integration in mammalian cells mediated by a new hybrid baculovirus-adeno-associated virus vector. J Virol. 1998; 72:5025-5034.
14. Smith R H. Adeno-associated virus integration: virus versus vector. Gene Ther. 2008; 15:817-822.
15. Berns K I, Kort J, Fife K H, Grogan E W, Spear I. Study of the fine structure of adeno-associated virus DNA with bacterial restriction endonucleases. J Virol. 1975; 16:712-719.
16. Cheung A K, Hoggan M D, Hauswirth W W, Berns K I. Integration of the adeno-associated virus genome into cellular DNA in latently infected human Detroit 6 cells. J Virol. 1980; 33:739-748.
17. Samulski R I, Chang L S, Shenk T. A recombinant plasmid from which an infectious adeno-associated virus genome can be excised in vitro and its use to study viral replication. J Virol. 1987; 61:3096-3101.
18. Recchia A, Perani L, Sartori D, Olgiati C, Mavilio F. Site-specific integration of functional transgenes into the human genome, by adeno/AAV hybrid vectors. Mol Ther. 2004; 10:660-670.
19. Zufferey R, Nagy D, Mandel R I, Naldini L, Trono D. Multiply attenuated lentiviral vector achieves efficient gene delivery in vivo. Nat Biotechnol. 1997; 15:871-875.
20. Follenzi A, Ailles L E, Bakovic S, Geuna M, Naldini L. Gene transfer by lentiviral vectors is limited by nuclear translocation and rescued by HIV-1 pol sequences. Nat Genet. 2000; 25:217-222.
21. Porcellini S, Alberici L, Gubinelli F, et al. The F12-Vif derivative Chim3 inhibits HIV-1 replication in CD4+ T lymphocytes and CD34+-derived macrophages by blocking HIV-1 DNA integration. Blood. 2009; 113:3443-3452.
22. Porcellini S, Gubinelli F, Alberici L, Piovani B M, Rizzardi G P, Bovolenta C. Chim3 confers survival advantage to CD4+ T cells upon HIV-1 infection by preventing HIV-1 DNA integration and HIV-1-induced G2 cell-cycle delay. Blood. 2010; 115:4021-4029.
23. Sandrin V, Boson B, Salmon P, et al. Lentiviral vectors pseudotyped with a modified RD114 envelope glycoprotein show increased stability in sera and augmented transduction of primary lymphocytes and CD34+ cells derived from human and nonhuman primates. Blood. 2002; 100: 823-832.
24. Di Nunzio F, Piovani B, Cosset F L, Mavilio F, Stornaiuolo A. Transduction of human hematopoietic stem cells by lentiviral vectors pseudotyped with the RD114-TR chimeric envelope glycoprotein. Hum Gene Ther. 2007; 18:811-820.
25. Dull, T., Zufferey, R., Kelly, M., Mandel, R. J., Nguyen, M., Trono, D., Naldini, L. A third-generation lentivirus vector with a conditional packaging system. J Virol, 1998; 72: 8463-71

The invention claimed is:

1. A system for stable expression of lentiviral structural and regulatory proteins consisting of:
   i. a hybrid vector comprising baculoviral backbone containing an integration cassette flanked by adeno-associated virus (AAV) inverted terminal repeats (ITRs) including two expression cassettes, wherein the first expression cassette encodes lentiviral gag and pol and the second cassette encodes lentiviral rev and a selection marker; and
   ii. an expression plasmid containing the AAV Rep Open Reading Frame (ORF) under the control of a promoter.

2. The system according to claim 1 wherein the two expression cassettes of the hybrid vector are tail to tail oriented and each one is driven by a constitutive promoter and comprise a poly A.

3. The system according to claim 1 wherein the promoter is selected from cytomegalovirus (CMV), CMV immediate-early (IE), phosphoglycerate kinase (PGK), simian virus 40 (SV40), elongation factor 1 alpha (eF1α), spleen focus-forming virus (SFFV), and rous sarcoma virus (RSV).

4. The system according to claim 1 wherein the promoter is a CMV IE promoter.

5. The system according to claim 1 wherein the selection marker is selected from a hygromycin, kanamycin, neomycin, and zeomycin resistance gene.

6. The system according to claim 5 wherein the selection marker is a hygromycin resistance gene.

7. The system according to claim 1 wherein the selection marker is cloned downstream from an internal ribosome entry site (IRES).

8. The system according to claim 1 wherein the rep protein is rep78.

9. A semi-stable lentiviral packaging cell line consisting of cells stably expressing lentiviral gag, pol and rev characterized in that such cells contain stably integrated into its genome at least one copy of an integration cassette flanked by AAV inverted terminal repeats (ITR) including two expression cassettes, wherein the first expression cassette encodes lentiviral gag and pol and the second cassette encodes lentiviral rev and a selection marker.

10. The semi-stable lentiviral packaging cell line according to claim 9 wherein the cell is a human cell line selected from HEK293, HEK293-T, HEK293-SF, TE671, HT1080 and HeLa.

11. The semi-stable lentiviral packaging cell line according to claim 9 wherein the two expression cassettes are tail to tail oriented and each one is driven by a constitutive promoter and comprise a poly A.

12. The semi-stable packaging cell line according to claim 9 wherein the promoter is selected from CMV, CMV IE, PGK, SV40, eF1α, SFFV and RSV.

13. The semi-stable packaging cell line according to claim 12 wherein the promoter is a CMV IE promoter.

14. The semi-stable packaging cell line according to claim 9 wherein the selection marker is selected from a hygromycin, kanamycin, neomycin, and zeomycin resistance gene.

15. The semi-stable packaging cell line according to claim 14 wherein the selection marker is a hygromycin resistance gene.

16. The semi-stable packaging cell line according to claim 9 wherein selection marker is cloned downstream an internal ribosome entry site (IRES).

17. A method for producing lentiviral vectors comprising:
   i. culturing a semi-stable packaging cell line according to claim 9;
   ii. inserting in the semi-stable packging cell line an env gene; and
   iii. inserting in the semi-stable packging cell line a transfer vector.

18. The method according to claim 17 wherein the env gene is selected from vesicular stomatitis virus-glycoprotein (VSV-G) env, murine leukemia virus (MLV) 4070 env, endogenous feline virus RD114 env, chimeric envelope protein RD114-TR, chimeric envelope protein RD114-pro, baculovirus GP64 env, and GALV env or derivatives thereof.

19. The method according to claim 17 wherein the env gene is the gene encoding the chimeric envelope protein RD114-TR.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer"
      /organism="artificial sequences"

<400> SEQUENCE: 1
cgggctgctg gcccaccagg                                              20

<210> SEQ ID NO 2
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="primer"
      /organism="artificial sequences"

<400> SEQUENCE: 2
atgccggggt tttacgagat tgtg                                         24

<210> SEQ ID NO 3
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 3
cttgaggagg tcttcgtcgc                                              20

<210> SEQ ID NO 4
<211> LENGTH: 21
<212> TYPE: DNA
<213> ORGANISM: artificial sequences
```

```
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 4
ccctgttact tctcccttc c                                              21

<210> SEQ ID NO 5
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 5
tgtctccgct tcttcctgcc                                               20

<210> SEQ ID NO 6
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 6
ttaaccatag aaaagaaggg g                                             21

<210> SEQ ID NO 7
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 7
acatcaagca gccatgcaaa t                                             21

<210> SEQ ID NO 8
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 8
atctggcctg gtgcaatagg                                               20

<210> SEQ ID NO 9
<211> LENGTH: 31
<212> TYPE: DNA
```

```
<213> ORGANISM: artificial sequences
<220> FEATURE:
<221> NAME/KEY: source
<222> LOCATION: 1..31
<223> OTHER INFORMATION: /mol_type="DNA"
      /note="probe"
      /organism="artificial sequences"

<400> SEQUENCE: 9
catcaatgag gaagctgcag aatgggatag a                              31

<210> SEQ ID NO 10
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 10
gtagcatggc gggttaatca                                           20

<210> SEQ ID NO 11
<211> LENGTH: 27
<212> TYPE: DNA
<213> ORGANISM: artificial sequences
<220> FEATURE:
<221> NAME/KEY: source
<222> LOCATION: 1..27
<223> OTHER INFORMATION: /mol_type="DNA"
      /note="primer"
      /organism="artificial sequences"

<400> SEQUENCE: 11
ttaactacaa ggaacccta gtgatgg                                    27

<210> SEQ ID NO 12
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 12
gtaatacgac tcactatagg gc                                        22

<210> SEQ ID NO 13
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="primer"
      /organism="artificial sequences"

<400> SEQUENCE: 13
agggctccgc ttaagggac                                            19

<210> SEQ ID NO 14
<211> LENGTH: 76
```

```
<212> TYPE: DNA
<213> ORGANISM: artificial sequences
<220> FEATURE:
<221> NAME/KEY: source
<222> LOCATION: 1..76
<223> OTHER INFORMATION: /mol_type="DNA"
      /note="linker sequence"
      /organism="artificial sequences"

<400> SEQUENCE: 14
gatcgtccct taagcggagc cctatagtga gtcgtattac cagggaattc gcctcgggat      60
atcactcagc ataatg                                                     76
```